(12) United States Patent
 Liu

(10) Patent No.: US 12,011,304 B2
(45) Date of Patent: Jun. 18, 2024

(54) FULL-BODY PET-CT COMBINED DEVICE

(71) Applicant: SHANDONG MADIC TECHNOLOGY CO., LTD., Linyi (CN)

(72) Inventor: Jiguo Liu, Linyi (CN)

(73) Assignee: SHANDONG MADIC TECHNOLOGY CO., LTD., Linyi (CN)

( * ) Notice: Subject to any disclaimer, the term of this patent is extended or adjusted under 35 U.S.C. 154(b) by 0 days.

(21) Appl. No.: 17/767,494

(22) PCT Filed: Oct. 23, 2019

(86) PCT No.: PCT/CN2019/112737
§ 371 (c)(1),
(2) Date: Apr. 8, 2022

(87) PCT Pub. No.: WO2021/068287
PCT Pub. Date: Apr. 15, 2021

(65) Prior Publication Data
US 2024/0074713 A1    Mar. 7, 2024

(30) Foreign Application Priority Data
Oct. 9, 2019    (CN) .......................... 201910955895.7

(51) Int. Cl.
*A61B 6/04* (2006.01)
*A61B 6/00* (2024.01)
(Continued)

(52) U.S. Cl.
CPC ............ *A61B 6/0407* (2013.01); *A61B 6/032* (2013.01); *A61B 6/037* (2013.01); *A61B 6/4417* (2013.01); *A61B 6/5241* (2013.01); *A61B 6/4208* (2013.01)

(58) Field of Classification Search
CPC ................................................... A61B 6/0407
See application file for complete search history.

(56) References Cited

U.S. PATENT DOCUMENTS 6,094,760 A * 8/2000 Nonaka ................ A61B 6/0487
5/601
2003/0078489 A1   4/2003 DeSilets et al.
(Continued)

FOREIGN PATENT DOCUMENTS

| CN | 202589551 U | 12/2012 |
|---|---|---|
| CN | 106691486 A | 5/2017 |

(Continued)

OTHER PUBLICATIONS

International Search Report dated May 29, 2020 received in International Application No. PCT/CN2019/112737.

*Primary Examiner* — Chih-Cheng Kao
(74) *Attorney, Agent, or Firm* — Scully, Scott, Murphy & Presser, P.C.

(57) ABSTRACT

A full-body PET-CT combined device (11), characterized by comprising a power source (2), an industrial personal computer (3), a PET machine (5), a CT machine (6), a detection bed (7), a lifting portion (8), and a linear sliding table (9). The CT machine (6) is provided with a CT detector (61) and a CT rack (62). The PET machine (5) consists of a bearing base (51), a barrel detector assembly (52), a top detector assembly (53), and a neck detector assembly (54). The detection bed (7) is horizontally disposed, and a tail portion (71) thereof is fixed to a lifting shaft (81) of the lifting portion (8). A horizontal lifting bottom plate (82) is fixed below the lifting portion (8). The linear sliding table (9) is horizontally placed below the detection bed (7), and the CT machine (6) is located between the PET machine (5) and the lifting portion (8). The combined device (11) further comprises an elongated base (111), with the power source (2) etc.

(Continued)

being sequentially fixed to the upper surface of the base (111). A barrel detector (521), the CT detector (61) and the detection bed (7) are coaxially and horizontally disposed. The CT rack (62) is used for supporting the CT detector (61). The positions of the PET machine (5) and the CT machine (6) can be exchanged.

12 Claims, 5 Drawing Sheets

(51) Int. Cl.
*A61B 6/03* (2006.01)
*A61B 6/42* (2024.01)

(56) References Cited

U.S. PATENT DOCUMENTS

| | | | |
|---|---|---|---|
| 2008/0173218 A1* | 7/2008 | Wang | A61B 6/0407 |
| | | | 108/43 |
| 2015/0115162 A1 | 4/2015 | Tashima et al. | |
| 2017/0181715 A1* | 6/2017 | Wang | A61B 6/0407 |

FOREIGN PATENT DOCUMENTS

| | | |
|---|---|---|
| CN | 107550512 A | 1/2018 |
| CN | 107595316 A | 1/2018 |

* cited by examiner

FULL-BODY PET-CT COMBINED DEVICE

TECHNICAL FIELD

The present disclosure belongs to the field of radiographic medical imaging apparatus, and relates to a whole-body PET-CT combined device.

BACKGROUND

PET is the most typical medical imaging method that collects oppositely reflected photoelectrons (generally referred to as true coincidence event LOR) and correspondingly analyzes to form images. It has a significantly stronger imaging ability than CT, can perform function, metabolism and receptor imaging, and is the gold standard for detecting human body on a molecular level. At present, the mainstream PET detection devices are similar to the popular CT, both of which are cylindrical. A length thereof is not too long. For example, it has a cylindrical shape with two open ends and a length which is at most ¼ to ⅕ of the length of the human body. On one hand, this is because a detection unit is expensive, and there are too many coincidence counting circuits, making the device too complicated; and on the one hand, it is also for the purpose of facilitating the human body to pass through and move.

In the prior art, there is a way of combining a PET machine with a CT machine for use. Generally, the PET machine and the CT machine are placed one behind the other approximately coaxially. After one detection is completed on a detection object, the PET machine and the CT machine can be moved to a detection bed of another device immediately, and another detection can be performed immediately. This combined use is actually a kind of continuous use, and it does not really achieve the effect of simultaneous detection by PET-CT and joint effective analysis of the detection object, so it is not a real combined use.

Considering that a core part of PET-CT, that is, an annular detection part, is short in length, whereas the human body or phantom as the detection object is generally long, for one detection object, it is very difficult to use PET and CT in the prior art together for detection. It can only be separate detections, and the time consumed is also a sum of the time of the two.

To sum up, there are the following defects in the prior art. First, there is no apparatus that can combine the detections of PET and CT into one at the same time. In essence, the detections are performed separately, and it is necessary that the time consumed is doubled, making it impossible to achieve the purpose of effectively reducing the time. Another problem is that for the whole-body detection of the human body, out of consideration for passability, the device is configured to have a barrel shape according to habitual thinking. On the premise of not increasing an axial length, an enclosed solid space angle is small, the sensitivity is insufficient, and the design of the short barrel type detector makes its sensitivity unable to meet the increasing medical detection requirements.

SUMMARY

In view of the above two problems existing in the prior art, that is, there is no apparatus that really combines the detections of PET and CT into one for simultaneous use, and the short barrel type PET detector has a small enclosed solid space angle and insufficient sensitivity, the present disclosure provides a targeted solution, namely, a whole-body PET-CT combined device and method. The method of the present application has two prominent advantages. First, the PET and CT whole-body detections can be truly performed simultaneously, and it only takes the time of one whole-body detection to obtain two kinds of whole-body detection data of PET and CT, thereby effectively improving the efficiency. Second, on the premise of satisfying the passability, brain PET or similar technologies is adopted, such as the applicant's previous application CN109846505A; however, the use of different specific methods to expand the solid space angle enclosed by the short barrel type PET detector (such as the abovementioned application) is greatly different from the prior art, and the installation and arrangement are more difficult. Compared with the relatively novel arrangement in structure, the present application continues to use main parts of the traditional barrel-shaped PET detector, and effectively improve the sensitivity under the condition that the structure is not changed much and the cost is not increased. By adding a neck detector and a top detector, the solid space angle enclosed by the detector is effectively increased, and the problem of insufficient sensitivity is alleviated. At the same time, the neck detector and the top detector can be raised and lowered, which can ensure that on the premise of enabling the detection object to pass, the sensitivity can be improved as much as possible properly according to the situation of the detection object by adjusting a height of the detector.

A whole-body PET-CT combined device includes a power source, an industrial computer, a PET machine, a CT machine, a detection bed, a lifting part, and a linear slide table.

The CT machine is provided with a CT detector and a CT frame, the CT detector is hollow cylindrical or approximately hollow cylindrical, and the PET machine is composed of a support seat, a barrel detector assembly, a top detector assembly, and a neck detector assembly; the detection bed is arranged horizontally, and a tail of the detection bed is fixed on a lifting shaft of the lifting part; a horizontal lifting bottom plate is fixed under the lifting part; the linear slide table is horizontally placed under the detection bed, and a top surface of the linear slide table is provided with a slide groove; a slide groove member is embedded in the slide groove, and a top surface of the slide groove member is threadingly connected and fixed to a bottom surface of the lifting bottom plate; the CT machine is located between the PET machine and the lifting part; the barrel detector assembly includes a barrel detector, and the barrel detector is arranged close to the CT detector.

Further, the power source supplies power to the industrial computer, the PET machine, the CT machine, the detection bed, and the lifting part; the combined device further includes a long-strip-shaped base which is a rectangular parallelepiped having a rectangular shape in a top view, and there are several pairs of universal wheels for support under the base; an upper surface of the base is a first upper surface, and the PET machine, the CT machine and the linear slide table are fixed on the first upper surface in sequence; the barrel detector and the CT detector are coaxially arranged and have a common first axis; axes of the CT detector, the barrel detector and the detection bed are all arranged to be horizontal; an axis of the detection bed is a second axis, and the second axis is parallel to the first axis; the CT detector is fixed on the CT frame; the barrel detector assembly further includes a barrel bracket; the top detector assembly includes a top detector and a top bracket; the neck detector assembly includes a neck detector and a neck bracket; the top detector and the neck detector are independently driven to ascend or descend by a motor; the top detector assembly is located on a side of the PET machine away from the CT machine, and the neck detector assembly is located on a side of the PET machine close to the CT machine; the support seat is a rectangular parallelepiped, an upper surface of the support seat is provided with an installation bottom plate, and an upper surface of the installation bottom plate is fixed with the barrel detector assembly, the top detector assembly and the neck detector assembly.

Further, the power source and the industrial computer are fixed on the upper surface of the base; a distance between the closest detector modules of the barrel detector and the CT detector is smaller than 30-50 cm; the installation bottom plate is fixed on the support seat through several evenly distributed screws, and the barrel bracket, the top bracket and the neck bracket are all threadingly connected and fixed to the installation bottom plate; each of the several pairs of universal wheels has a separate stop mechanism; and the barrel bracket includes a left support bracket and a right support bracket.

The top bracket includes a first front guide column, a first rear guide column, a first front ball screw, a first rear ball screw, a first photosensor, a first plate, a second plate, a first motor, a first coupling, a first synchronous belt, and a first synchronous pulley; the second plate is parallel to the first plate and is located under the first plate; the first front guide column, the first rear guide column, the first front ball screw and the first rear ball screw are all perpendicular to the installation bottom plate; the first coupling is sleeved over a shaft of the first motor, and the first synchronous belt is connected with the first synchronous pulley and the first coupling and is kept in tension; the first photosensor is hoisted under the first plate, the top detector is fixed under the second plate, and a detection surface of the top detector faces the direction of the barrel detector.

The neck bracket includes a third front guide column, a third rear guide column, a third front ball screw, a third rear ball screw, a second photosensor, a third plate, a fourth plate, a second motor, a second coupling, a second synchronous belt and a second synchronous pulley; the fourth plate is parallel to the third plate and is located under the third plate; the third front guide column, the third rear guide column, the third front ball screw and the third rear ball screw are all perpendicular to the installation bottom plate; the second coupling is sleeved over a shaft of the second motor, and the second synchronous belt is connected with the second synchronous pulley and the second coupling and is kept in tension; the second photosensor is hoisted under the third plate, the neck detector is fixed under the fourth plate, and a detection surface of the neck detector faces the direction of the barrel detector.

Further, the left support bracket includes an upper left support bracket, a lower left support bracket, a first left rod, and a second left rod, and the right support bracket includes an upper right support bracket, a lower right support bracket, a first right rod, and a second right rod; a left side of the lower left support bracket is provided with a plurality of support wings that are perpendicular to a plane of the lower left support bracket, and a left side of the lower right support bracket is provided with a plurality of support wings that are perpendicular to a plane of the lower right support bracket; lower sides of the upper left support bracket and the upper right support bracket and upper sides of the lower left support bracket and the lower right support bracket are all arc-shaped for matching with an outer surface of the barrel detector; upper and lower ends of the first left rod are respectively threadingly connected with left ends of the upper left support bracket and the lower left support bracket, and upper and lower ends of the second left rod are respectively threadingly connected with right ends of the upper left support bracket and the lower left support bracket; upper and lower ends of the first right rod are respectively threadingly connected with left ends of the upper right support bracket and the lower right support bracket, and upper and lower ends of the second right rod are respectively threadingly connected with left ends of the upper right support bracket and the lower right support bracket.

The first front ball screw is located on a rear side of the first front guide column, and the first rear ball screw is located on a front side of the first rear guide column; upper ends of the first front guide column and the first rear guide column are fixed to front and rear ends of the first plate; an upper end of the first front ball screw passes through the first plate and the second plate and is connected with the shaft of the first motor; the first front ball screw cooperates with a first front nut seat on the second plate; an upper end of the first rear ball screw passes through the first plate and the second plate and is connected with a shaft of the first synchronous pulley, and the first rear ball screw cooperates with a first rear nut seat on the second plate.

The third front ball screw is located on a rear side of the third front guide column, and the third rear ball screw is located on a front side of the third rear guide column; upper ends of the third front guide column and the third rear guide column are fixed to front and rear ends of the third plate; an upper end of the third front ball screw passes through the third plate and the fourth plate and is connected with the shaft of the second motor; the third front ball screw cooperates with a third front nut seat on the fourth plate; an upper end of the third rear ball screw passes through the third plate and the fourth plate and is connected with a shaft of the second synchronous pulley, and the third rear ball screw cooperates with a third rear nut seat on the fourth plate.

The first photosensor and the second photosensor each include a photosensor array of a plurality of sensor units, and each sensor unit obtains a response time by capturing a reflected signal.

The present application also claims a whole-body PET-CT combined detection method, which is performed by using the aforementioned whole-body PET-CT combined device, and which includes the following steps: 1) using a position where the top detector is completely lowered as a first detection position, setting a second detection position where the top detector is partially lowered, using a position where the neck detector is completely lowered as a third detection position, setting a fourth detection position where the neck detector is partially lowered, and setting a head position in the barrel detector; 2) placing an object on the detection bed with a head end of the object facing the direction of the PET machine; adjusting a height of the detection bed using the lifting part so that the object is approximately coaxial with the CT detector and the barrel detector; putting the PET machine and the CT machine into a standby state, translating the detection bed toward the direction of the PET machine until the head end of the object enters the CT machine, and using the CT detector to detect and record data; 3) moving a part of the object that has been detected by CT completely out of the CT detector, using the CT detector to detect the next part of the object, and performing these operations repeatedly; 4) lowering the top detector to the first detection position and lowering the neck detector to the third detection position when the head end of the object moves to the head position, so as to perform PET detection and at the same time also perform CT detection; raising the top detector to the second detection position, and raising the neck detector to the fourth detection position; 5) moving a part of the object that has been detected by PET completely out of the barrel detector, performing PET detection and also performing CT detection at the same time, and performing these operations repeatedly until the object is completely moved out of the PET machine from the other side; and 6) recording all the PET data and CT data obtained, and calculating whole-body PET image data and whole-body CT image data.

Further, when in the first detection position, all the detection surfaces of the top detector are completely exposed, and when in the third detection position, all the detection surfaces of the neck detector are completely exposed; the object being approximately coaxial with the CT detector and the barrel detector means that the coaxiality of the three is within 3-5 mm; the height of the detection bed is adjusted by the lifting part by means of manual rotation or electronically controlled hydraulic pressure; the timing when the head end of the object moves to the head position is obtained by naked eye observation or by photoelectric switch detection; when calculating the whole-body PET image data and the whole-body CT image data, specifically, for each PET detection and CT detection, an image is obtained separately and a relative position of front and rear ends of the object corresponding to the image is recorded, and only one of the overlapping image parts is reserved, thus generating whole-body image data.

A whole-body PET-CT combined device includes a power source, an industrial computer, a PET machine, a CT machine, a detection bed, a lifting part, and a linear slide table.

The CT machine is provided with a CT detector and a CT frame, the CT detector is hollow cylindrical or approximately hollow cylindrical, and the PET machine is composed of a support seat, a barrel detector assembly, a top detector assembly, and a neck detector assembly; the detection bed is arranged horizontally, and a tail of the detection bed is fixed on a lifting shaft of the lifting part; a horizontal lifting bottom plate is fixed under the lifting part; the linear slide table is horizontally placed under the detection bed, and a top surface of the linear slide table is provided with a slide groove; a slide groove member is embedded in the slide groove, and a top surface of the slide groove member is threadingly connected and fixed to a bottom surface of the lifting bottom plate; the PET machine is located between the CT machine and the lifting part, the barrel detector assembly includes a barrel detector, and the barrel detector is arranged close to the CT detector.

Further, the power source supplies power to the industrial computer, the PET machine, the CT machine, the detection bed, and the lifting part.

Further, the combined device further includes a long-strip-shaped base which is a rectangular parallelepiped having a rectangular shape in a top view, and there are several pairs of universal wheels for support under the base; an upper surface of the base is a first upper surface, and the CT machine, the PET machine and the linear slide table are fixed on the first upper surface in sequence.

Further, the barrel detector and the CT detector are coaxially arranged and have a common first axis; axes of the CT detector, the barrel detector and the detection bed are all arranged to be horizontal; an axis of the detection bed is a second axis, and the second axis is parallel to the first axis; the CT detector is fixed on the CT frame.

Further, the barrel detector assembly further includes a barrel bracket; the top detector assembly includes a top detector and a top bracket; the neck detector assembly includes a neck detector and a neck bracket; the top detector and the neck detector are independently driven to ascend or descend by a motor; the top detector assembly is located on a side of the PET machine close to the CT machine, and the neck detector assembly is located on a side of the PET machine away from the CT machine.

Further, the support seat is a rectangular parallelepiped, an upper surface of the support seat is provided with an installation bottom plate, and an upper surface of the installation bottom plate is fixed with the barrel detector assembly, the top detector assembly and the neck detector assembly.

Further, the power source and the industrial computer are fixed on the upper surface of the base; a distance between the closest detector modules of the barrel detector and the CT detector is smaller than 30-50 cm.

The installation bottom plate is fixed on the support seat through several evenly distributed screws, and the barrel bracket, the top bracket and the neck bracket are all threadingly connected and fixed to the installation bottom plate.

Each of the several pairs of universal wheels has a separate stop mechanism; and the barrel bracket includes a left support bracket and a right support bracket.

The top bracket includes a first front guide column, a first rear guide column, a first front ball screw, a first rear ball screw, a first photosensor, a first plate, a second plate, a first motor, a first coupling, a first synchronous belt, and a first synchronous pulley; the second plate is parallel to the first plate and is located under the first plate; the first front guide column, the first rear guide column, the first front ball screw and the first rear ball screw are all perpendicular to the installation bottom plate; the first coupling is sleeved over a shaft of the first motor, and the first synchronous belt is connected with the first synchronous pulley and the first coupling and is kept in tension; the first photosensor is hoisted under the first plate, the top detector is fixed under the second plate, and a detection surface of the top detector faces the direction of the barrel detector.

The neck bracket includes a third front guide column, a third rear guide column, a third front ball screw, a third rear ball screw, a second photosensor, a third plate, a fourth plate, a second motor, a second coupling, a second synchronous belt and a second synchronous pulley; the fourth plate is parallel to the third plate and is located under the third plate; the third front guide column, the third rear guide column, the third front ball screw and the third rear ball screw are all perpendicular to the installation bottom plate; the second coupling is sleeved over a shaft of the second motor, and the second synchronous belt is connected with the second synchronous pulley and the second coupling and is kept in tension; the second photosensor is hoisted under the third plate, the neck detector is fixed under the fourth plate, and a detection surface of the neck detector faces the direction of the barrel detector.

Further, the left support bracket includes an upper left support bracket, a lower left support bracket, a first left rod, and a second left rod, and the right support bracket includes an upper right support bracket, a lower right support bracket, a first right rod, and a second right rod; a left side of the lower left support bracket is provided with a plurality of support wings that are perpendicular to a plane of the lower left support bracket, and a left side of the lower right support bracket is provided with a plurality of support wings that are perpendicular to a plane of the lower right support bracket; lower sides of the upper left support bracket and the upper right support bracket and upper sides of the lower left support bracket and the lower right support bracket are all arc-shaped for matching with an outer surface of the barrel detector; upper and lower ends of the first left rod are respectively threadingly connected with left ends of the upper left support bracket and the lower left support bracket, and upper and lower ends of the second left rod are respectively threadingly connected with right ends of the upper left support bracket and the lower left support bracket; upper and lower ends of the first right rod are respectively threadingly connected with left ends of the upper right support bracket and the lower right support bracket, and upper and lower ends of the second right rod are respectively threadingly connected with left ends of the upper right support bracket and the lower right support bracket.

The first front ball screw is located on a rear side of the first front guide column, and the first rear ball screw is located on a front side of the first rear guide column; upper ends of the first front guide column and the first rear guide column are fixed to front and rear ends of the first plate; an upper end of the first front ball screw passes through the first plate and the second plate and is connected with the shaft of the first motor; the first front ball screw cooperates with a first front nut seat on the second plate; an upper end of the first rear ball screw passes through the first plate and the second plate and is connected with a shaft of the first synchronous pulley, and the first rear ball screw cooperates with a first rear nut seat on the second plate.

The third front ball screw is located on a rear side of the third front guide column, and the third rear ball screw is located on a front side of the third rear guide column; upper ends of the third front guide column and the third rear guide column are fixed to front and rear ends of the third plate; an upper end of the third front ball screw passes through the third plate and the fourth plate and is connected with the shaft of the second motor; the third front ball screw cooperates with a third front nut seat on the fourth plate; an upper end of the third rear ball screw passes through the third plate and the fourth plate and is connected with a shaft of the second synchronous pulley, and the third rear ball screw cooperates with a third rear nut seat on the fourth plate.

The first photosensor and the second photosensor each include a photosensor array of a plurality of sensor units, and each sensor unit obtains a response time by capturing a reflected signal.

A whole-body PET-CT combined detection method is provided, which is performed by using the aforementioned whole-body PET-CT combined device, and which includes the following steps: 1) using a position where the top detector is completely lowered as a first detection position, setting a second detection position where the top detector is partially lowered, using a position where the neck detector is completely lowered as a third detection position, setting a fourth detection position where the neck detector is partially lowered, and setting a head position in the barrel detector; 2) placing an object on the detection bed with a head end of the object facing the direction of the PET machine; adjusting a height of the detection bed using the lifting part so that the object is approximately coaxial with the CT detector and the barrel detector; and putting the PET machine and the CT machine into a standby state; 3) translating the detection bed toward the direction of the PET machine until the head end of the object reaches the head position in the PET machine, lowering the top detector to the first detection position and lowering the neck detector to the third detection position, so as to perform PET detection; 4) raising the top detector to the second detection position, and raising the neck detector to the fourth detection position; 5) moving a part of the object that has been detected by PET completely out of the PET detector, detecting the next part of the object using the PET detector, and when any part of the object is located in the CT machine at the same time of PET detection, performing CT detection simultaneously; and performing these operations repeatedly until the object is completely moved out of the CT machine from the other side; and 6) recording all the PET data and CT data obtained, and calculating whole-body PET image data and whole-body CT image data.

Further, when in the first detection position, all the detection surfaces of the top detector are completely exposed, and when in the third detection position, all the detection surfaces of the neck detector are completely exposed; the object being approximately coaxial with the CT detector and the barrel detector means that the coaxiality of the three is within 3-5 mm; the height of the detection bed is adjusted by the lifting part by means of manual rotation or electronically controlled hydraulic pressure; the timing when the head end of the object moves to the head position is obtained by naked eye observation or by photoelectric switch detection; when calculating the whole-body PET image data and the whole-body CT image data, specifically, for each PET detection and CT detection, an image is obtained separately and a relative position of front and rear ends of the object corresponding to the image is recorded, and only one of the overlapping image parts is reserved, thus generating whole-body image data.

The advantages of the present disclosure are presented as follows. (1): The difficulty of arrangement and manufacture is low. The top detector and the neck detector are planar detectors, and the barrel detector is a common cylindrical detector; when they are combined, the manufacture and design processes are not very complicated and are easy to implement, but a similar effect to the whole-body PET apparatus can also be achieved; the difficulty of design and manufacture is extremely lower than a complex device that requires a five-axis apparatus for manufacture. 2): Time is saved. One-time pass of the detection object is realized, that is, the whole-body PET image and the whole-body CT image that can previously be obtained only during at least two periods of time can now be obtained during one period of time. 3): By making the heights of the barrel and the neck positions adjustable, when performing PET detection on the head of the detection object, the problem of insufficient sensitivity of the existing whole-body apparatus when detecting the head is solved; and when detecting other parts, the barrel detector and the neck detector are slightly raised, so that at the same time of ensuring the passability, some detectors of the barrel and neck detectors still work, which ensures that the detection space angle is larger than that of an ordinary apparatus, and the sensitivity is also higher than that of an ordinary apparatus.

BRIEF DESCRIPTION OF THE DRAWINGS

In order to illustrate the embodiments of the present disclosure or the technical solutions in the prior art more clearly, the accompanying drawings that are required to be used in describing the embodiments or the prior art will be introduced briefly in the following. Obviously, the drawings in the following description only illustrate some embodiments of the present disclosure. For those skilled in the art, other drawings can also be obtained according to these drawings without creative efforts.

Components corresponding to reference signs: 11: whole-body PET-CT combined device; 12: PET detector; 13: PET machine base; 14: PET detection bed; 15: CT detector; 16: CT machine base; 17: CT detection bed; 2: power source; 3: industrial computer; 5: PET machine; 6: CT machine; 7: detection bed; 8: lifting part; 9: linear slide table;

51: support seat; 511: installation bottom plate; 52: barrel detector assembly; 521: barrel detector; 522: barrel bracket; 53: top detector assembly; 531: top detector; 532: top bracket; 54: neck detector assembly; 541: neck detector; 542: neck detector; 5320: first front guide column; 5321: first rear guide column; 5322: first front ball screw; 5323: first rear ball screw; 5324: first photosensor; 5325: first plate; 5326: second plate; 5327: first motor; 5328: first coupling; 5329: first synchronous belt; 5330: first synchronous pulley; 5420: third front guide column; 5421: third rear guide column; 5422: third front ball screw; 5423: third rear ball screw; 5424: second photosensor; 5425: third plate; 5426: fourth plate; 5427: second motor; 5428: second coupling; 5429: second synchronous belt; 5430: second synchronous pulley; 55: left support bracket; 550: upper left support bracket; 551: lower left support bracket; 552: first left rod; 553: second left rod; 56: right support bracket; 560: upper right support bracket; 561: lower right support bracket; 562: first right rod; 563: second right rod; 57: support wing; 61: CT detector; 62: CT frame; 71: tail; 81: lifting shaft; 82: lifting bottom plate; 91: chute; 92: slide groove member.

DETAILED DESCRIPTION

Preferred embodiments of the present disclosure will be described in detail below with reference to the accompanying drawings, so that the advantages and features of the present disclosure can be more easily understood by those skilled in the art, and the scope of protection of the present disclosure can be more clearly defined.

Figure 1:
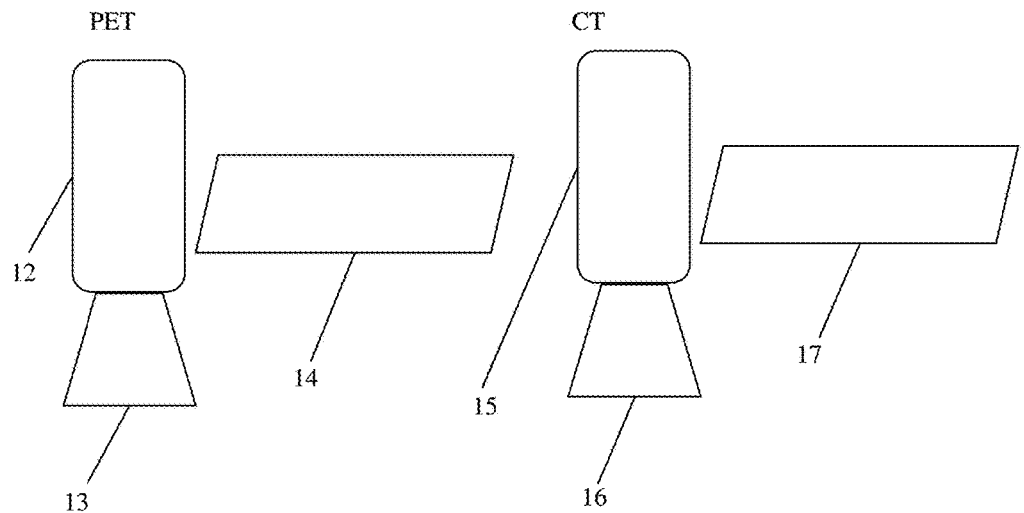
FIG. 1 is a view of CT and PET apparatuses in the prior art.

A common CT machine and PET machine are shown in FIG. 1. Due to the bulky auxiliary frame, it is impossible for them to detect simultaneously. Even if they are put together for use, CT detection and PET detection are performed separately.

First Embodiment

Figure 2:
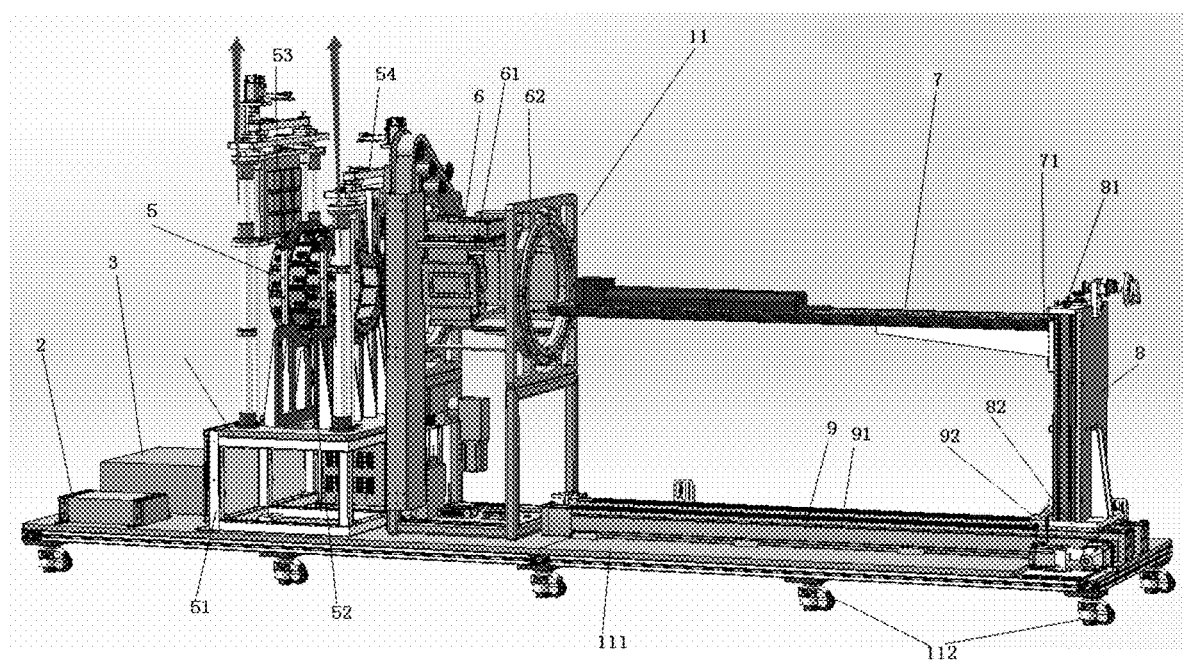
FIG. 2 is a full view of a combined device of the present application.
Figure 3:
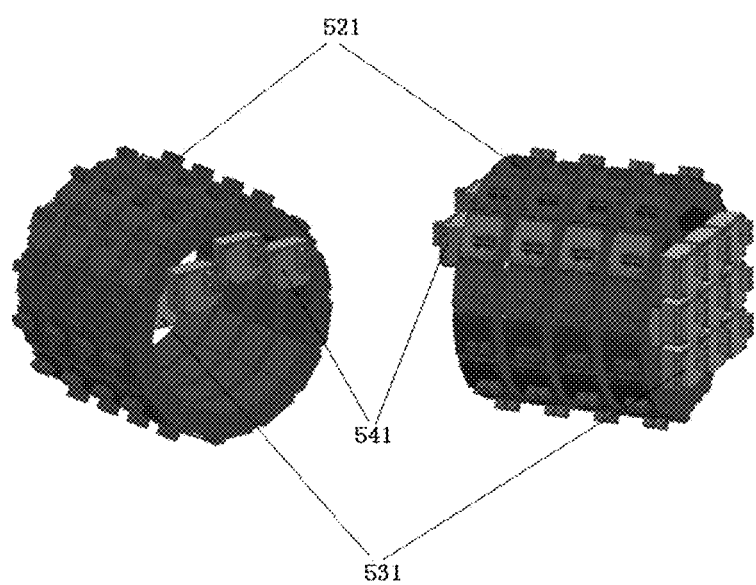
FIG. 3 is a schematic view of a barrel detector, a top detector, and a neck detector.
Figure 4:
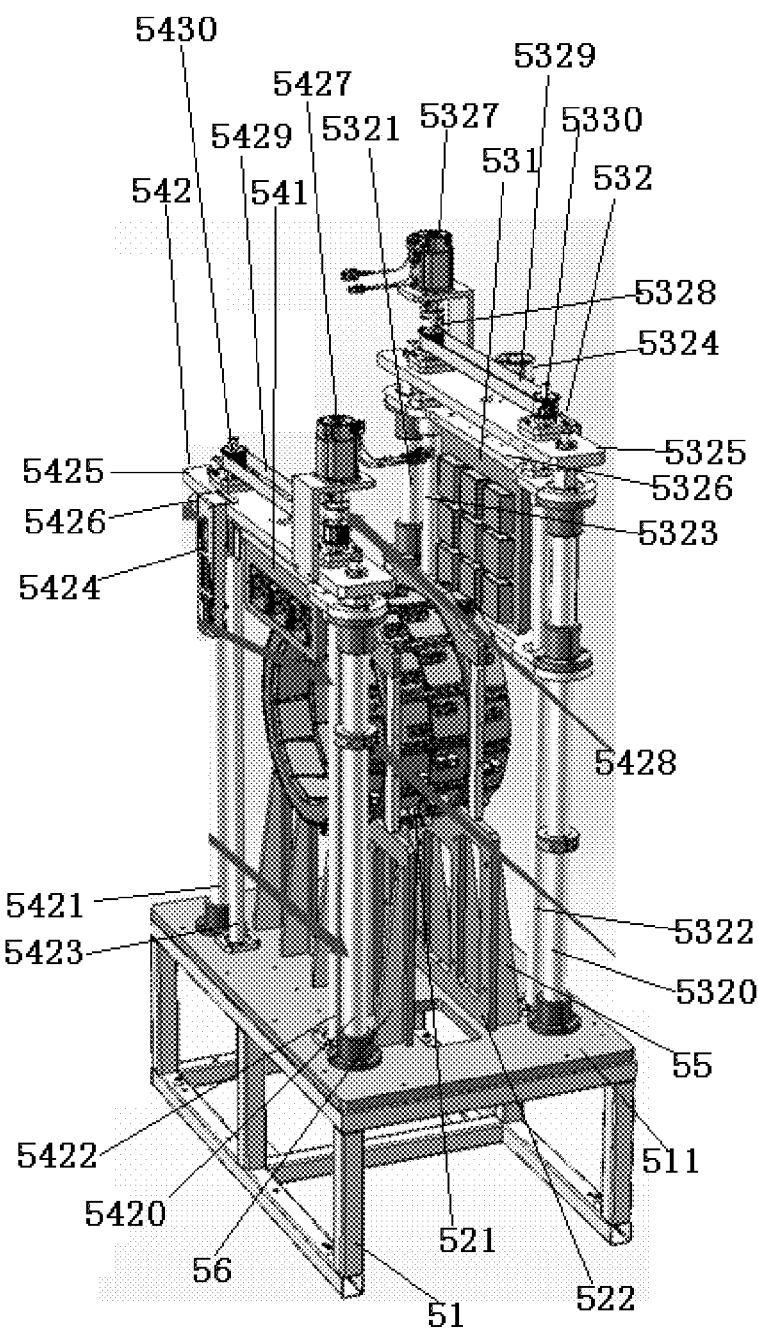
FIG. 4 is a schematic view of various components of a PET machine.
Figure 5:
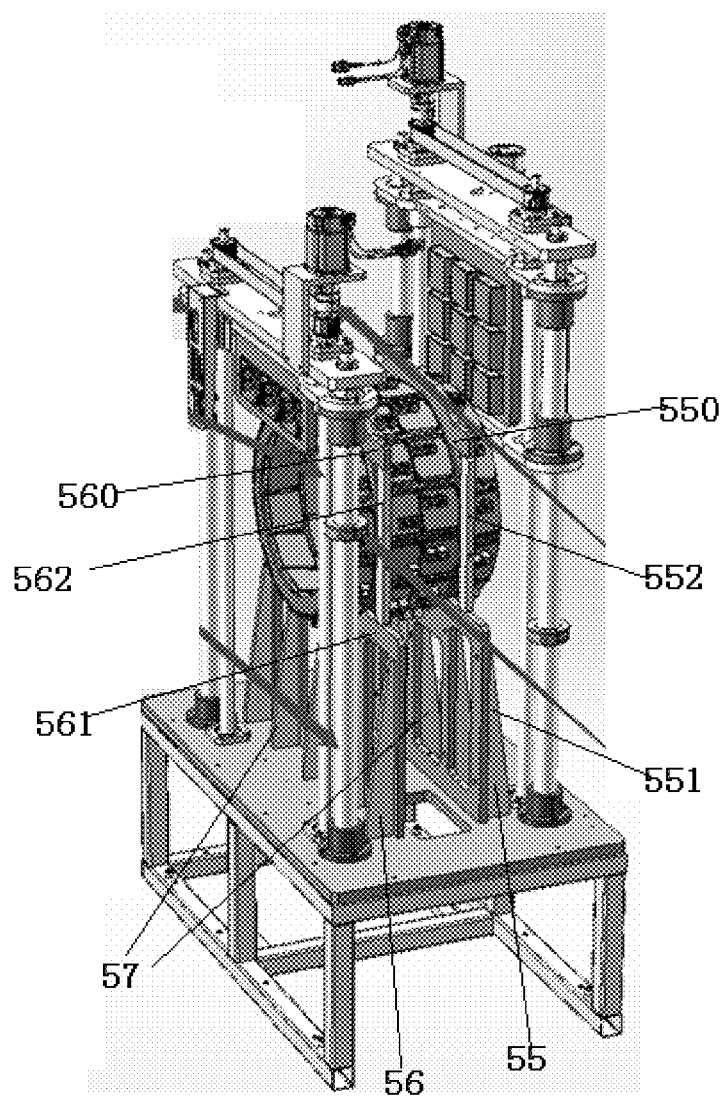
FIG. 5 is a schematic view of a barrel bracket.
Figure 6:
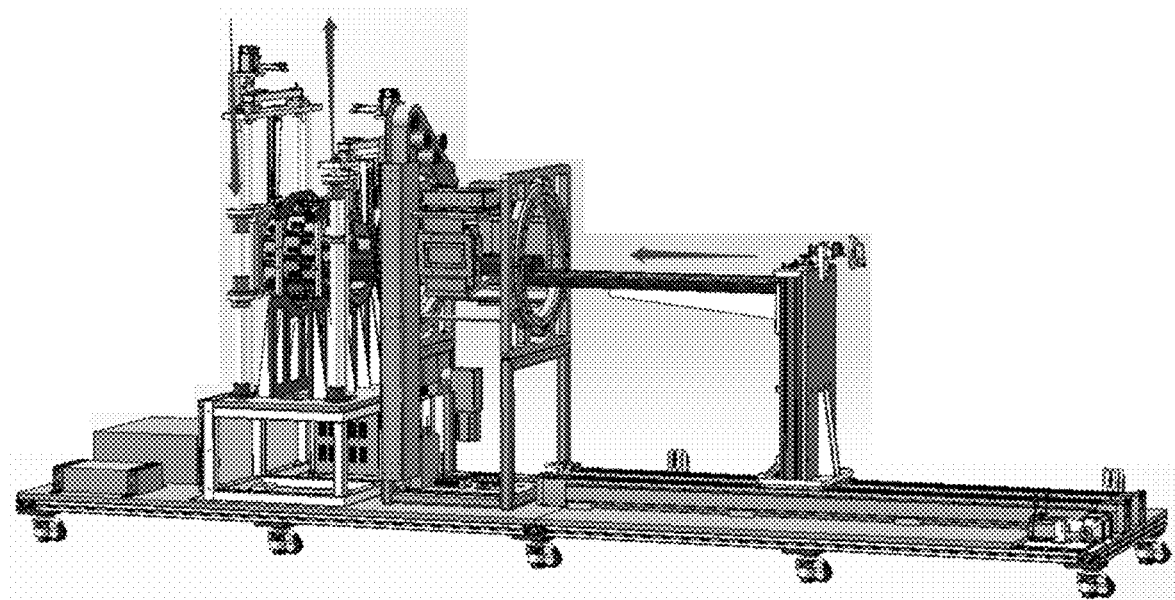
FIG. 6 is a schematic view illustrating detection of a head of a detection object.
Figure 7:
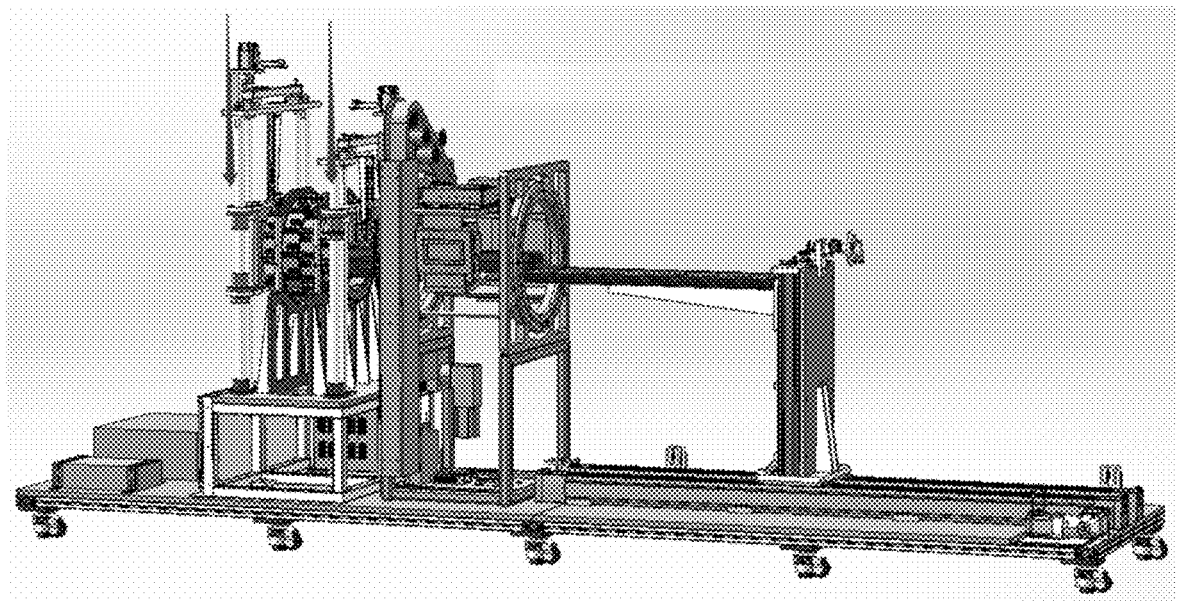
FIG. 7 is a schematic view illustrating detection of a body of the detection object.

A whole-body PET-CT combined device 11 includes a power source 2, an industrial computer 3, a PET machine 5, a CT machine 6, a detection bed 7, a lifting part 8, and a linear slide table 9. In this embodiment, the industrial computer and the power source are arranged on one side of a base 111, and then the PET machine 5, the CT machine 6, and the detection bed 7 are arranged in sequence. When in use, a detection object first enters the CT machine, and then enters the PET machine, until the detection object completely exits the PET machine from the other side, so that the detection is accomplished. At this time, the detection bed is completely moved out in a reverse direction, and the detection is ended, as shown in FIGS. 2, 6 and 7.

The CT machine 6 is provided with a CT detector 61 and a CT frame 62, and the CT detector is hollow cylindrical or approximately hollow cylindrical; the PET machine 5 is composed of a support seat 51, a barrel detector assembly 52, a top detector assembly 53, and a neck detector assembly 54; the detection bed 7 is arranged horizontally, and a tail 71 of the detection bed 7 is fixed on a lifting shaft 81 of the lifting part 8; a horizontal lifting bottom plate 82 is fixed under the lifting part 8; the linear slide table 9 is horizontally placed under the detection bed 7, and a top surface of the linear slide table 9 is provided with a slide groove 91; a slide groove member 92 is embedded in the slide groove 91, and a top surface of the slide groove member 92 is threadingly connected and fixed to a bottom surface of the lifting bottom plate 82; the CT machine 6 is located between the PET machine 5 and the lifting part 8; the barrel detector assembly 52 includes a barrel detector 521, and the barrel detector 521 is arranged close to the CT detector 61. The CT detector may be a general barrel-shaped CT detector. The detectors in the barrel detector assembly 52, the top detector assembly 53 and the neck detector assembly 54 are all composed of PET detection modules having square or rectangular detection surfaces. The detection modules on the barrel detector 521 all face inward; the detection modules on the top detector 531 all face the direction of the barrel detector 521 and are substantially perpendicular to an axis of the barrel detector 521, and the detection modules on the top detector 531 may be divided into a plurality of rows, such as 3-6 rows of modules from top to bottom; the detection modules on the neck detector 541 all face the direction of the barrel detector 521 and are substantially perpendicular to the axis of the barrel detector 521, and the detection modules on the top detector 541 may be divided into a plurality of rows, such as 1-6 rows of modules from top to bottom.

Further, the power source 2 supplies power to the industrial computer 3, the PET machine 5, the CT machine 6, the detection bed 7, and the lifting part 8; the combined device 11 also includes a long-strip-shaped base 111 which is a rectangular parallelepiped having a rectangular shape in a top view, and there are several pairs of universal wheels 112 for support under the base; each universal wheel is provided with a stop switch; an upper surface of the base is a first upper surface 1111 which is, for example, made of solid wood or MDF; the PET machine 5, the CT machine 6 and the linear slide table 9 are fixed on the first upper surface 1111 in sequence; the barrel detector 521 and the CT detector 61 are coaxially arranged and have a common first axis 112, or have a coaxiality within 5 mm; axes of the CT detector 61, the barrel detector 521 and the detection bed 7 are all arranged to be horizontal; an axis of the detection bed is a second axis 113, and the second axis 112 is parallel to the first axis 113; the CT detector 61 is fixed on the CT frame 62; the barrel detector assembly 52 further includes a barrel bracket 522; the top detector assembly 53 includes a top detector 531 and a top bracket 532; the neck detector assembly 54 includes a neck detector 541 and a neck bracket 542; the top detector 531 and the neck detector 541 are independently driven to ascend or descend by a motor, and the motor drives a lead screw to rotate, whereas the top detector 531 and the neck detector 541 are respectively installed on a second plate and a fourth plate that cooperate with the lead screw; the top detector assembly 53 is located on a side of the PET machine 5 away from the CT machine 6, and the neck detector assembly 54 is located on a side of the PET machine 5 close to the CT machine 6; the support seat 51 is a rectangular parallelepiped, an upper surface of the support seat 51 is provided with an installation bottom plate 511, and an upper surface of the installation bottom plate 511 is fixed with the barrel detector assembly 52, the top detector assembly 53 and the neck detector assembly 54. The installation bottom plate 511 is, for example, made of solid wood or engineering plastic, and is suitable for tight engagement with screws, so that the barrel detector assembly 52, the top detector assembly 53 and the neck detector assembly 54 can also be firmly fixed.

Further, the power source 2 and the industrial computer 3 are fixed on the upper surface of the base 111; a distance between the closest detector modules of the barrel detector 521 and the CT detector 61 is smaller than 30-50 cm. Herein, the distance is defined to ensure that the gap between the barrel detector 521 and the other two detectors is not too large. The installation bottom plate 511 is fixed on the support seat 51 through several evenly distributed screws, such as more than 12 screws at centrally symmetrical positions. The barrel bracket 522, the top bracket 532 and the neck bracket 542 are all threadingly connected and fixed to the installation bottom plate 511; each of the several pairs of universal wheels 112 has a separate stop mechanism; and the barrel bracket 522 includes a left support bracket 55 and a right support bracket 56.

The top bracket 532 includes a first front guide column 5320, a first rear guide column 5321, a first front ball screw 5322, a first rear ball screw 5323, a first photosensor 5324, a first plate 5325, a second plate 5326, a first motor 5327, a first coupling 5328, a first synchronous belt 5329, and a first synchronous pulley 5330; the second plate 5326 is parallel to the first plate 5325 and is located under the first plate 5325; the first front guide column 5320, the first rear guide column 5321, the first front ball screw 5322 and the first rear ball screw 5323 are all perpendicular to the installation bottom plate 511; the first coupling 5328 is sleeved over a shaft of the first motor 5327, and the first synchronous belt 5329 is connected with the first synchronous pulley 5330 and the first coupling 5328 and is kept in tension; the first photosensor 5324 is hoisted under the first plate 5325, the top detector 531 is fixed under the second plate 5326, and a detection surface of the top detector 531 faces the direction of the barrel detector 521. When the first motor 5327 rotates, the first front ball screw 5322 rotates with it, and the first rear ball screw 5323 also rotates with it through power transmission, thus driving the second plate 5326 to ascend or descend, so that the top detector 531 also ascends or descends with the second plate 5326.

The neck bracket 542 includes a third front guide column 5420, a third rear guide column 5421, a third front ball screw 5422, a third rear ball screw 5423, a second photosensor 5424, a third plate 5425, a fourth plate 5426, a second motor 5427, a second coupling 5428, a second synchronous belt 5429 and a second synchronous pulley 5430; the fourth plate 5426 is parallel to the third plate 5425 and is located under the third plate 5425; the third front guide column 5420, the third rear guide column 5421, the third front ball screw 5422 and the third rear ball screw 5423 are all perpendicular to the installation bottom plate 511; the second coupling 5428 is sleeved over a shaft of the second motor 5427, and the second synchronous belt 5429 is connected with the second synchronous pulley 5430 and the second coupling 5428 and is kept in tension; the second photosensor 5424 is hoisted under the third plate 5425, the neck detector 541 is fixed under the fourth plate 5426, and a detection surface of the neck detector 541 faces the direction of the barrel detector 521. When the second motor 5427 rotates, the first front ball screw 5422 rotates with it, and the first rear ball screw 5423 also rotates with it through power transmission, thus driving the fourth plate 5426 to ascend or descend, so that the neck detector 541 also ascends or descends with the fourth plate 5426.

Further, the left support bracket 55 includes an upper left support bracket 550, a lower left support bracket 551, a first left rod 552, and a second left rod 553, and the right support bracket 56 includes an upper right support bracket 560, a lower right support bracket 561, a first right rod 562, and a second right rod 563; a left side of the lower left support bracket 551 is provided with a plurality of support wings 57 that are perpendicular to a plane of the lower left support bracket 551, and a left side of the lower right support bracket 561 is provided with a plurality of support wings 57 that are perpendicular to a plane of the lower right support bracket 561; lower sides of the upper left support bracket 550 and the upper right support bracket 560 and upper sides of the lower left support bracket 551 and the lower right support bracket 561 are all arc-shaped for matching with an outer surface of the barrel detector 521; upper and lower ends of the first left rod 552 are respectively threadingly connected with left ends of the upper left support bracket 550 and the lower left support bracket 551, and upper and lower ends of the second left rod 553 are respectively threadingly connected with right ends of the upper left support bracket 550 and the lower left support bracket 551; upper and lower ends of the first right rod 562 are respectively threadingly connected with left ends of the upper right support bracket 560 and the lower right support bracket 561, and upper and lower ends of the second right rod 563 are respectively threadingly connected with left ends of the upper right support bracket 560 and the lower right support bracket 561. The left support bracket 55 and the right support bracket 56 are in left-and-right mirror symmetry with each other, and jointly fix the barrel detector 521.

The first front ball screw 5322 is located on a rear side of the first front guide column 5320, and the first rear ball screw 5323 is located on a front side of the first rear guide column 5321; upper ends of the first front guide column 5320 and the first rear guide column 5321 are fixed to front and rear ends of the first plate 5325; an upper end of the first front ball screw 5322 passes through the first plate 5325 and the second plate 5326 and is connected with the shaft of the first motor 5327; the first front ball screw 5322 cooperates with a first front nut seat on the second plate 5326; an upper end of the first rear ball screw 5323 passes through the first plate 5325 and the second plate 5326 and is connected with a shaft of the first synchronous pulley 5330, and the first rear ball screw 5323 cooperates with a first rear nut seat on the second plate 5326.

The third front ball screw 5422 is located on a rear side of the third front guide column 5420, and the third rear ball screw 5423 is located on a front side of the third rear guide column 5421; upper ends of the third front guide column 5420 and the third rear guide column 5421 are fixed to front and rear ends of the third plate 5425; an upper end of the third front ball screw 5422 passes through the third plate 5425 and the fourth plate 5426 and is connected with the shaft of the second motor 5427; the third front ball screw 5422 cooperates with a third front nut seat on the fourth plate 5426; an upper end of the third rear ball screw 5423 passes through the third plate 5425 and the fourth plate 5426 and is connected with a shaft of the second synchronous pulley 5430, and the third rear ball screw 5423 cooperates with a third rear nut seat on the fourth plate 5426.

The first photosensor 5324 and the second photosensor 5424 each include a photosensor array of a plurality of sensor units, and each sensor unit obtains a response time by capturing a reflected signal. The first photosensor 5324 and the second photosensor 5424 are, for example, a plurality of reflective photosensors arranged from top to bottom. They determine the positions of lower edges of the neck detector 541 and the top detector 531 by capturing whether there is a reflected signal, and on this basis, determine the actual positions of the neck detector 541 and the top detector 531, and which detection modules on the neck detector 541 and the top detector 531 are completely exposed respectively. The signals collected by the first photosensor 5324 and the second photosensor 5424 can be introduced into a coincidence circuit for calculation.

Second Embodiment

In this embodiment, the device of the first embodiment is used for detection, that is, a combined device of a PET machine 5, a CT machine 6 and a detection bed 7 arranged in sequence is used. A whole-body PET-CT combined detection method, which is performed by using the whole-body PET-CT combined device of the first embodiment, includes the following steps: 1) using a position where the top detector is completely lowered as a first detection position, setting a second detection position where the top detector is partially lowered, using a position where the neck detector is completely lowered as a third detection position, setting a fourth detection position where the neck detector is partially lowered, and setting a head position in the barrel detector; 2) placing an object on the detection bed with a head end of the object facing the direction of the PET machine; adjusting a height of the detection bed using the lifting part so that the object is approximately coaxial with the CT detector and the barrel detector; putting the PET machine and the CT machine into a standby state, translating the detection bed toward the direction of the PET machine until the head end of the object enters the CT machine, and using the CT detector to detect and record data; 3) moving a part of the object that has been detected by CT completely out of the CT detector, using the CT detector to detect the next part of the object, and performing these operations repeatedly; 4) lowering the top detector to the first detection position and lowering the neck detector to the third detection position when the head end of the object moves to the head position, so as to perform PET detection and at the same time also perform CT detection; raising the top detector to the second detection position, and raising the neck detector to the fourth detection position; 5) moving a part of the object that has been detected by PET completely out of the barrel detector, performing PET detection and also performing CT detection at the same time, and performing these operations repeatedly until the object is completely moved out of the PET machine from the other side; and 6) recording all the PET data and CT data obtained, and calculating whole-body PET image data and whole-body CT image data.

Preferably, when in the first detection position, all the detection surfaces of the top detector are completely exposed, and when in the third detection position, all the detection surfaces of the neck detector are completely exposed; herein, all the detection surfaces refer to detection surfaces of comprehensive detection modules. For the second detection position and the fourth detection position, due to the different passability of the detection object, there can be a plurality of choices. If there are N rows of detection modules on the top detector and M rows of detection modules on the neck detector, then the second detection position may correspond to a state in which 1 to N−1 rows of detection modules are exposed, that is, there are N−1 choices for the second detection position, and the fourth detection position may correspond to a state in which 1 to M−1 rows of detection modules are exposed, that is, there are M−1 choices for the fourth detection position. Specifically, for example, there are 5 choices for the second detection position of the top detector, and 3 choices for the fourth detection position of the neck detector.

The object being approximately coaxial with the CT detector and the barrel detector means that the coaxiality of the three is within 3-5 mm; and the height of the detection bed is adjusted by the lifting part by means of manual rotation or electronically controlled hydraulic pressure. On the premise of being adapted to the lead screw, the manual rotation controls the lifting part to ascend or descend through rotation. In case of electronically controlled hydraulic pressure, for example, an inner rod of a hydraulic rod is fixedly connected to the detection bed, and the inner rod can be inserted downward into an outer rod, or the inner rod can move upward out of the outer rod, so as to control the ascending or descending of the lifting part.

The timing when the head end of the object moves to the head position is obtained by naked eye observation or by photoelectric switch detection; and the photoelectric switch is, for example, a reflective photosensor.

When calculating the whole-body PET image data and the whole-body CT image data, specifically, for each PET detection and CT detection, an image is obtained separately and a relative position of front and rear ends of the object corresponding to the image is recorded, and only one of the overlapping image parts is reserved, thus generating whole-body image data. The reason for the overlapping images is that in step 4, when the head of the object moves to the head position, it is very difficult to be just the case where the part of the image that has been detected by the CT has been completely moved out of the CT machine; therefore, in most cases, the images will be partially overlapping.

Third Embodiment

A whole-body PET-CT combined device 11 includes a power source 2, an industrial computer 3, a PET machine 5, a CT machine 6, a detection bed 7, a lifting part 8, and a linear slide table 9. In this embodiment, the industrial computer and the power source are arranged in any position of a base 111, such as on one side, and then the CT machine 6, the PET machine 5, and the detection bed 7 are arranged in sequence. When in use, a detection object first enters the PET machine, and then enters the CT machine, until the detection object completely exits the CT machine from the other side, so that the detection is accomplished. At this time, the detection bed is completely moved out in a reverse direction, and the detection is ended. Despite the different arrangement, this order can also achieve joint detection and save time. different from FIG. 2, the positions of the PET machine and the CT machine have exchanged.

The CT machine 6 is provided with a CT detector 61 and a CT frame 62, and the CT detector is hollow cylindrical or approximately hollow cylindrical; the PET machine 5 is composed of a support seat 51, a barrel detector assembly 52, a top detector assembly 53, and a neck detector assembly 54; the detection bed 7 is arranged horizontally, and a tail 71 of the detection bed 7 is fixed on a lifting shaft 81 of the lifting part 8; a horizontal lifting bottom plate 82 is fixed under the lifting part 8; the linear slide table 9 is horizontally placed under the detection bed 7, and a top surface of the linear slide table 9 is provided with a slide groove 91; a slide groove member 92 is embedded in the slide groove 91, and a top surface of the slide groove member 92 is threadingly connected and fixed to a bottom surface of the lifting bottom plate 82; the PET machine 5 is located between the CT machine 6 and the lifting part 8; the barrel detector assembly 52 includes a barrel detector 521, and the barrel detector 521 is arranged close to the CT detector 61. The CT detector may be a general barrel-shaped CT detector. The detectors in the barrel detector assembly 52, the top detector assembly 53 and the neck detector assembly 54 are all composed of PET detection modules having square or rectangular detection surfaces. The detection modules on the barrel detector 521 all face inward; the detection modules on the top detector 531 all face the direction of the barrel detector 521 and are substantially perpendicular to an axis of the barrel detector 521, and the detection modules on the top detector 531 may be divided into a plurality of rows, such as 3-6 rows of modules from top to bottom; the detection modules on the neck detector 541 all face the direction of the barrel detector 521 and are substantially perpendicular to the axis of the barrel detector 521, and the detection modules on the top detector 541 may be divided into a plurality of rows, such as 1-6 rows of modules from top to bottom.

Further, the power source 2 supplies power to the industrial computer 3, the PET machine 5, the CT machine 6, the detection bed 7, and the lifting part 8; the combined device 11 also includes a long-strip-shaped base 111 which is a rectangular parallelepiped having a rectangular shape in a top view, and there are several pairs of universal wheels 112 for support under the base; each universal wheel is provided with a stop switch; an upper surface of the base is a first upper surface 1111 which is, for example, made of solid wood or MDF; the CT machine 6, the PET machine 5 and the linear slide table 9 are fixed on the first upper surface 1111 in sequence; the barrel detector 521 and the CT detector 61 are coaxially arranged and have a common first axis 112, or have a coaxiality within 5 mm; axes of the CT detector 61, the barrel detector 521 and the detection bed 7 are all arranged to be horizontal; an axis of the detection bed is a second axis 113, and the second axis 112 is parallel to the first axis 113; the CT detector 61 is fixed on the CT frame 62; the barrel detector assembly 52 further includes a barrel bracket 522; the top detector assembly 53 includes a top detector 531 and a top bracket 532; the neck detector assembly 54 includes a neck detector 541 and a neck bracket 542; the top detector 531 and the neck detector 541 are independently driven to ascend or descend by a motor, and the motor drives a lead screw to rotate, whereas the top detector 531 and the neck detector 541 are respectively installed on a second plate and a fourth plate that cooperate with the lead screw; the top detector assembly 53 is located on a side of the PET machine 5 close to the CT machine 6, and the neck detector assembly 54 is located on a side of the PET machine 5 away from the CT machine 6; the support seat 51 is a rectangular parallelepiped, an upper surface of the support seat 51 is provided with an installation bottom plate 511, and an upper surface of the installation bottom plate 511 is fixed with the barrel detector assembly 52, the top detector assembly 53 and the neck detector assembly 54. The installation bottom plate 511 is, for example, made of solid wood or engineering plastic, and is suitable for tight engagement with screws, so that the barrel detector assembly 52, the top detector assembly 53 and the neck detector assembly 54 can also be firmly fixed.

Further, the power source 2 and the industrial computer 3 are fixed on the upper surface of the base 111; a distance between the closest detector modules of the barrel detector 521 and the CT detector 61 is smaller than 30-50 cm. Herein, the distance is defined to ensure that the gap between the barrel detector 521 and the other two detectors is not too large. The installation bottom plate 511 is fixed on the support seat 51 through several evenly distributed screws, such as more than 12 screws at centrally symmetrical positions. The barrel bracket 522, the top bracket 532 and the neck bracket 542 are all threadingly connected and fixed to the installation bottom plate 511; each of the several pairs of universal wheels 112 has a separate stop mechanism; and the barrel bracket 522 includes a left support bracket 55 and a right support bracket 56.

The configurations of the top bracket 532, the neck bracket 542, the barrel bracket, the left support bracket 55 and the right support bracket 56 are the same as those in the first embodiment.

The first photosensor 5324 and the second photosensor 5424 each include a photosensor array of a plurality of sensor units, and each sensor unit obtains a response time by capturing a reflected signal. The first photosensor 5324 and the second photosensor 5424 are, for example, a plurality of reflective photosensors arranged from top to bottom. They determine the positions of lower edges of the neck detector 541 and the top detector 531 by capturing whether there is a reflected signal, and on this basis, determine the actual positions of the neck detector 541 and the top detector 531, and which detection modules on the neck detector 541 and the top detector 531 are completely exposed respectively. The signals collected by the first photosensor 5324 and the second photosensor 5424 can be introduced into a coincidence circuit for calculation.

Fourth Embodiment

In this embodiment, the device of the third embodiment is used for detection, that is, a combined device of a CT machine 6, a PET machine 5 and a detection bed 7 arranged in sequence is used. A whole-body PET-CT combined detection method, which is performed by using the whole-body PET-CT combined device of the first embodiment, includes the following steps: 1) using a position where the top detector is completely lowered as a first detection position, setting a second detection position where the top detector is partially lowered, using a position where the neck detector is completely lowered as a third detection position, setting a fourth detection position where the neck detector is partially lowered, and setting a head position in the barrel detector; 2) placing an object on the detection bed with a head end of the object facing the direction of the PET machine; adjusting a height of the detection bed using the lifting part so that the object is approximately coaxial with the CT detector and the barrel detector; and putting the PET machine and the CT machine into a standby state; 3) translating the detection bed toward the direction of the PET machine until the head end of the object reaches the head position in the PET machine, lowering the top detector to the first detection position and lowering the neck detector to the third detection position, so as to perform PET detection; 4) raising the top detector to the second detection position, and raising the neck detector to the fourth detection position; 5) moving a part of the object that has been detected by PET completely out of the PET detector, detecting the next part of the object using the PET detector, and when any part of the object is located in the CT machine at the same time of PET detection, performing CT detection simultaneously; and performing these operations repeatedly until the object is completely moved out of the CT machine from the other side; and 6) recording all the PET data and CT data obtained, and calculating whole-body PET image data and whole-body CT image data.

Preferably, when in the first detection position, all the detection surfaces of the top detector are completely exposed, and when in the third detection position, all the detection surfaces of the neck detector are completely exposed; herein, all the detection surfaces refer to detection surfaces of comprehensive detection modules. For the second detection position and the fourth detection position, due to the different passability of the detection object, there can be a plurality of choices. If there are N rows of detection modules on the top detector and M rows of detection modules on the neck detector, then the second detection position may correspond to a state in which 1 to N−1 rows of detection modules are exposed, that is, there are N−1 choices for the second detection position, and the fourth detection position may correspond to a state in which 1 to M−1 rows of detection modules are exposed, that is, there are M−1 choices for the fourth detection position. Specifically, for example, there are 5 choices for the second detection position of the top detector, and 3 choices for the fourth detection position of the neck detector.

The object being approximately coaxial with the CT detector and the barrel detector means that the coaxiality of the three is within 3-5 mm; and the height of the detection bed is adjusted by the lifting part by means of manual rotation or electronically controlled hydraulic pressure. On the premise of being adapted to the lead screw, the manual rotation controls the lifting part to ascend or descend through rotation. In case of electronically controlled hydraulic pressure, for example, an inner rod of a hydraulic rod is fixedly connected to the detection bed, and the inner rod can be inserted downward into an outer rod, or the inner rod can move upward out of the outer rod, so as to control the ascending or descending of the lifting part.

The timing when the head end of the object moves to the head position is obtained by naked eye observation or by photoelectric switch detection; and the photoelectric switch is, for example, a reflective photosensor.

When calculating the whole-body PET image data and the whole-body CT image data, specifically, for each PET detection and CT detection, an image is obtained separately and a relative position of front and rear ends of the object corresponding to the image is recorded, and only one of the overlapping image parts is reserved, thus generating whole-body image data. The reason for the overlapping images is that in step 4, when the head of the object moves to the head position, it is very difficult to be just the case where the part of the image that has been detected by the CT has been completely moved out of the CT machine; therefore, in most cases, the images will be partially overlapping.

Fifth Embodiment

The embodiment will be further described with reference to FIG. 6 and FIG. 7. For steps 1-6 in the second embodiment, in addition to lowering the top detector only when the head end of the object reaches the head position in step 4, it is also possible to lower the top detector completely and raise the neck detector completely at the beginning. At this time, the timing when the head end of the object reaches the head position in the PET needs to be determined by visual observation. When the head end of the object reaches a predetermined position, the neck detector can be lowered. When the neck detector reaches the third detection position and the top detector is in the first detection position, the head can be detected with a higher sensitivity, and the detection effect is obviously stronger than that of only using the barrel detector. After this, the neck detector can be raised to the fourth detection position, and the top detector can be raised to the second detection position, so that the whole body of the object can pass through for subsequent detection.

Described above are only preferred specific embodiments of the present disclosure, but the scope of protection of the present disclosure is not limited thereto. Any change or replacement that can be easily conceived by those skilled in the art within the technical scope disclosed in the present disclosure shall be covered within the scope of protection of the present disclosure. Therefore, the scope of protection of the present disclosure shall be subject to the scope of protection of the claims.

The invention claimed is:

1. A whole-body PET-CT combined device, comprising:
a power source, an industrial computer, a PET machine, a CT machine, a detection bed, a lifting part, and a linear slide table;
wherein the CT machine is provided with a CT detector and a CT frame, and the CT detector is hollow cylindrical or approximately hollow cylindrical;
the PET machine is composed of a support seat, a barrel detector assembly, a top detector assembly, and a neck detector assembly;
the detection bed is arranged horizontally, and a tail of the detection bed is fixed on a lifting shaft of the lifting part;
a horizontal lifting bottom plate is fixed under the lifting part;
the linear slide table is horizontally placed under the detection bed, a top surface of the linear slide table is provided with a slide groove, a slide groove member is embedded in the slide groove, and a top surface of the slide groove member is threadingly connected and fixed to a bottom surface of the lifting bottom plate; and
the CT machine is located between the PET machine and the lifting part, the barrel detector assembly comprises a barrel detector, and the barrel detector is arranged close to the CT detector.

2. The whole-body PET-CT combined device according to claim 1, wherein:
the power source supplies power to the industrial computer, the PET machine, the CT machine, the detection bed, and the lifting part;
the combined device further comprises a long-strip-shaped base which is a rectangular parallelepiped having a rectangular shape in a top view, and there are several pairs of universal wheels for support under the base; an upper surface of the base is a first upper surface, and the PET machine, the CT machine and the linear slide table are fixed on the first upper surface in sequence;
the barrel detector and the CT detector are coaxially arranged and have a common first axis; axes of the CT detector, the barrel detector and the detection bed are all arranged to be horizontal; an axis of the detection bed is a second axis, and the second axis is parallel to the first axis; the CT detector is fixed on the CT frame;
the barrel detector assembly further comprises a barrel bracket; the top detector assembly comprises a top detector and a top bracket; the neck detector assembly comprises a neck detector and a neck bracket; the top detector and the neck detector are independently driven to ascend or descend by a motor; the top detector assembly is located on a side of the PET machine away from the CT machine, and the neck detector assembly is located on a side of the PET machine close to the CT machine; and the support seat is a rectangular parallelepiped, an upper surface of the support seat is provided with an installation bottom plate, and an upper surface of the installation bottom plate is fixed with the barrel detector assembly, the top detector assembly and the neck detector assembly.

3. The whole-body PET-CT combined device according to claim 2, wherein:

the power source and the industrial computer are fixed on the upper surface of the base; a distance between the closest detector modules of the barrel detector and the CT detector is smaller than 30-50 cm;

the installation bottom plate is fixed on the support seat through several evenly distributed screws, and the barrel bracket, the top bracket and the neck bracket are all threadingly connected and fixed to the installation bottom plate;

each of the several pairs of universal wheels has a separate stop mechanism;

the barrel bracket comprises a left support bracket and a right support bracket;

the top bracket comprises a first front guide column, a first rear guide column, a first front ball screw, a first rear ball screw, a first photosensor, a first plate, a second plate, a first motor, a first coupling, a first synchronous belt, and a first synchronous pulley; the second plate is parallel to the first plate and is located under the first plate; the first front guide column, the first rear guide column, the first front ball screw and the first rear ball screw are all perpendicular to the installation bottom plate; the first coupling is sleeved over a shaft of the first motor, and the first synchronous belt is connected with the first synchronous pulley and the first coupling and is kept in tension; the first photosensor is hoisted under the first plate, the top detector is fixed under the second plate, and a detection surface of the top detector faces the direction of the barrel detector;

the neck bracket comprises a third front guide column, a third rear guide column, a third front ball screw, a third rear ball screw, a second photosensor, a third plate, a fourth plate, a second motor, a second coupling, a second synchronous belt and a second synchronous pulley;

the fourth plate is parallel to the third plate and is located under the third plate; the third front guide column, the third rear guide column, the third front ball screw and the third rear ball screw are all perpendicular to the installation bottom plate; the second coupling is sleeved over a shaft of the second motor, and the second synchronous belt is connected with the second synchronous pulley and the second coupling and is kept in tension; the second photosensor is hoisted under the third plate, the neck detector is fixed under the fourth plate, and a detection surface of the neck detector faces the direction of the barrel detector.

4. The whole-body PET-CT combined device according to claim 3, wherein:

the left support bracket comprises an upper left support bracket, a lower left support bracket, a first left rod, and a second left rod, and the right support bracket comprises an upper right support bracket, a lower right support bracket, a first right rod, and a second right rod; a left side of the lower left support bracket is provided with a plurality of support wings that are perpendicular to a plane of the lower left support bracket, and a left side of the lower right support bracket is provided with a plurality of support wings that are perpendicular to a plane of the lower right support bracket; lower sides of the upper left support bracket and the upper right support bracket and upper sides of the lower left support bracket and the lower right support bracket are all arc-shaped for matching with an outer surface of the barrel detector; upper and lower ends of the first left rod are respectively threadingly connected with left ends of the upper left support bracket and the lower left support bracket, and upper and lower ends of the second left rod are respectively threadingly connected with right ends of the upper left support bracket and the lower left support bracket; upper and lower ends of the first right rod are respectively threadingly connected with left ends of the upper right support bracket and the lower right support bracket, and upper and lower ends of the second right rod are respectively threadingly connected with left ends of the upper right support bracket and the lower right support bracket;

the first front ball screw is located on a rear side of the first front guide column, and the first rear ball screw is located on a front side of the first rear guide column; upper ends of the first front guide column and the first rear guide column are fixed to front and rear ends of the first plate; an upper end of the first front ball screw passes through the first plate and the second plate and is connected with the shaft of the first motor; the first front ball screw cooperates with a first front nut seat on the second plate; an upper end of the first rear ball screw passes through the first plate and the second plate and is connected with a shaft of the first synchronous pulley, and the first rear ball screw cooperates with a first rear nut seat on the second plate;

the third front ball screw is located on a rear side of the third front guide column, and the third rear ball screw is located on a front side of the third rear guide column; upper ends of the third front guide column and the third rear guide column are fixed to front and rear ends of the third plate; an upper end of the third front ball screw passes through the third plate and the fourth plate and is connected with the shaft of the second motor; the third front ball screw cooperates with a third front nut seat on the fourth plate; an upper end of the third rear ball screw passes through the third plate and the fourth plate and is connected with a shaft of the second synchronous pulley, and the third rear ball screw cooperates with a third rear nut seat on the fourth plate; and the first photosensor and the second photosensor each comprise a photosensor array of a plurality of sensor units, and each sensor unit obtains a response time by capturing a reflected signal.

5. A whole-body PET-CT combined detection method, which is performed by using the whole-body PET-CT combined device according to claim 2 4, wherein the method comprises the following steps:

1) using a position where the top detector is completely lowered as a first detection position, setting a second detection position where the top detector is partially lowered, using a position where the neck detector is completely lowered as a third detection position, setting a fourth detection position where the neck detector is partially lowered, and setting a head position in the barrel detector;

2) placing an object on the detection bed with a head end of the object facing the direction of the PET machine;

adjusting a height of the detection bed using the lifting part so that the object is approximately coaxial with the CT detector and the barrel detector; putting the PET machine and the CT machine into a standby state, translating the detection bed toward the direction of the PET machine until the head end of the object enters the CT machine, and using the CT detector to detect and record data;

3) moving a part of the object that has been detected by CT completely out of the CT detector, using the CT detector to detect the next part of the object, and performing these operations repeatedly;

4) lowering the top detector to the first detection position and lowering the neck detector to the third detection position when the head end of the object moves to the head position, so as to perform PET detection and at the same time also perform CT detection; raising the top detector to the second detection position, and raising the neck detector to the fourth detection position;

5) moving a part of the object that has been detected by PET completely out of the barrel detector, performing PET detection and also performing CT detection at the same time, and performing these operations repeatedly until the object is completely moved out of the PET machine from the other side; and 6) recording all the PET data and CT data obtained, and calculating whole-body PET image data and whole-body CT image data.

6. The whole-body PET-CT combined detection method according to claim 5, wherein:

when in the first detection position, all the detection surfaces of the top detector are completely exposed, and when in the third detection position, all the detection surfaces of the neck detector are completely exposed;

the object being approximately coaxial with the CT detector and the barrel detector means that the coaxiality of the three is within 3-5 mm;

the height of the detection bed is adjusted by the lifting part by means of manual rotation or electronically controlled hydraulic pressure;

the timing when the head end of the object moves to the head position is obtained by naked eye observation or by photoelectric switch detection;

when calculating the whole-body PET image data and the whole-body CT image data, specifically, for each PET detection and CT detection, an image is obtained separately and a relative position of front and rear ends of the object corresponding to the image is recorded, and only one of the overlapping image parts is reserved, thus generating whole-body image data.

7. A whole-body PET-CT combined device, comprising:
a power source, an industrial computer, a PET machine, a CT machine, a detection bed, a lifting part, and a linear slide table,
wherein the CT machine is provided with a CT detector and a CT frame, and the CT detector is hollow cylindrical or approximately hollow cylindrical;
the PET machine is composed of a support seat, a barrel detector assembly, a top detector assembly, and a neck detector assembly;
the detection bed is arranged horizontally, and a tail of the detection bed is fixed on a lifting shaft of the lifting part;
a horizontal lifting bottom plate is fixed under the lifting part;

the linear slide table is horizontally placed under the detection bed, a top surface of the linear slide table is provided with a slide groove, a slide groove member is embedded in the slide groove, and a top surface of the slide groove member is threadingly connected and fixed to a bottom surface of the lifting bottom plate; and
the PET machine is located between the CT machine and the lifting part, the barrel detector assembly comprises a barrel detector, and the barrel detector is arranged close to the CT detector.

8. The whole-body PET-CT combined device according to claim 7, wherein:

the power source supplies power to the industrial computer, the PET machine, the CT machine, the detection bed, and the lifting part;

the combined device further comprises a long-strip-shaped base which is a rectangular parallelepiped having a rectangular shape in a top view, and there are several pairs of universal wheels for support under the base; an upper surface of the base is a first upper surface, and the CT machine, the PET machine and the linear slide table are fixed on the first upper surface in sequence;

the barrel detector and the CT detector are coaxially arranged and have a common first axis; axes of the CT detector, the barrel detector and the detection bed are all arranged to be horizontal; an axis of the detection bed is a second axis, and the second axis is parallel to the first axis; the CT detector is fixed on the CT frame;

the barrel detector assembly further comprises a barrel bracket; the top detector assembly comprises a top detector and a top bracket; the neck detector assembly comprises a neck detector and a neck bracket; the top detector and the neck detector are independently driven to ascend or descend by a motor; the top detector assembly is located on a side of the PET machine close to the CT machine, and the neck detector assembly is located on a side of the PET machine away from the CT machine; and the support seat is a rectangular parallelepiped, an upper surface of the support seat is provided with an installation bottom plate, and an upper surface of the installation bottom plate is fixed with the barrel detector assembly, the top detector assembly and the neck detector assembly.

9. The whole-body PET-CT combined device according to claim 8, wherein:

the power source and the industrial computer are fixed on the upper surface of the base; a distance between the closest detector modules of the barrel detector and the CT detector is smaller than 30-50 cm;

the installation bottom plate is fixed on the support seat through several evenly distributed screws, and the barrel bracket, the top bracket and the neck bracket are all threadingly connected and fixed to the installation bottom plate;

each of the several pairs of universal wheels has a separate stop mechanism;

the barrel bracket comprises a left support bracket and a right support bracket;

the top bracket comprises a first front guide column, a first rear guide column, a first front ball screw, a first rear ball screw, a first photosensor, a first plate, a second plate, a first motor, a first coupling, a first synchronous belt, and a first synchronous pulley; the second plate is parallel to the first plate and is located under the first plate; the first front guide column, the first rear guide column, the first front ball screw and the first rear ball screw are all perpendicular to the installation bottom plate; the first coupling is sleeved over a shaft of the first motor, and the first synchronous belt is connected with the first synchronous pulley and the first coupling and is kept in tension; the first photosensor is hoisted under the first plate, the top detector is fixed under the second plate, and a detection surface of the top detector faces the direction of the barrel detector; and the neck bracket comprises a third front guide column, a third rear guide column, a third front ball screw, a third rear ball screw, a second photosensor, a third plate, a fourth plate, a second motor, a second coupling, a second synchronous belt and a second synchronous pulley;

the fourth plate is parallel to the third plate and is located under the third plate; the third front guide column, the third rear guide column, the third front ball screw and the third rear ball screw are all perpendicular to the installation bottom plate; the second coupling is sleeved over a shaft of the second motor, and the second synchronous belt is connected with the second synchronous pulley and the second coupling and is kept in tension; the second photosensor is hoisted under the third plate, the neck detector is fixed under the fourth plate, and a detection surface of the neck detector faces the direction of the barrel detector.

10. The whole-body PET-CT combined device according to claim 9, wherein:

the left support bracket comprises an upper left support bracket, a lower left support bracket, a first left rod, and a second left rod, and the right support bracket comprises an upper right support bracket, a lower right support bracket, a first right rod, and a second right rod;

a left side of the lower left support bracket is provided with a plurality of support wings that are perpendicular to a plane of the lower left support bracket, and a left side of the lower right support bracket is provided with a plurality of support wings that are perpendicular to a plane of the lower right support bracket; lower sides of the upper left support bracket and the upper right support bracket and upper sides of the lower left support bracket and the lower right support bracket are all arc-shaped for matching with an outer surface of the barrel detector; upper and lower ends of the first left rod are respectively threadingly connected with left ends of the upper left support bracket and the lower left support bracket, and upper and lower ends of the second left rod are respectively threadingly connected with right ends of the upper left support bracket and the lower left support bracket; upper and lower ends of the first right rod are respectively threadingly connected with left ends of the upper right support bracket and the lower right support bracket, and upper and lower ends of the second right rod are respectively threadingly connected with left ends of the upper right support bracket and the lower right support bracket;

the first front ball screw is located on a rear side of the first front guide column, and the first rear ball screw is located on a front side of the first rear guide column; upper ends of the first front guide column and the first rear guide column are fixed to front and rear ends of the first plate; an upper end of the first front ball screw passes through the first plate and the second plate and is connected with the shaft of the first motor; the first front ball screw cooperates with a first front nut seat on the second plate; an upper end of the first rear ball screw passes through the first plate and the second plate and is connected with a shaft of the first synchronous pulley, and the first rear ball screw cooperates with a first rear nut seat on the second plate;

the third front ball screw is located on a rear side of the third front guide column, and the third rear ball screw is located on a front side of the third rear guide column; upper ends of the third front guide column and the third rear guide column are fixed to front and rear ends of the third plate; an upper end of the third front ball screw passes through the third plate and the fourth plate and is connected with the shaft of the second motor; the third front ball screw cooperates with a third front nut seat on the fourth plate; an upper end of the third rear ball screw passes through the third plate and the fourth plate and is connected with a shaft of the second synchronous pulley, and the third rear ball screw cooperates with a third rear nut seat on the fourth plate;

the first photosensor and the second photosensor each comprise a photosensor array of a plurality of sensor units, and each sensor unit obtains a response time by capturing a reflected signal.

11. A whole-body PET-CT combined detection method, which is performed by using the whole-body PET-CT combined device according to claim 8, wherein the method comprises the following steps:

1) using a position where the top detector is completely lowered as a first detection position, setting a second detection position where the top detector is partially lowered, using a position where the neck detector is completely lowered as a third detection position, setting a fourth detection position where the neck detector is partially lowered, and setting a head position in the barrel detector;

2) placing an object on the detection bed with a head end of the object facing the direction of the PET machine; adjusting a height of the detection bed using the lifting part so that the object is approximately coaxial with the CT detector and the barrel detector; and putting the PET machine and the CT machine into a standby state;

3) translating the detection bed toward the direction of the PET machine until the head end of the object reaches the head position in the PET machine, lowering the top detector to the first detection position and lowering the neck detector to the third detection position, so as to perform PET detection;

4) raising the top detector to the second detection position, and raising the neck detector to the fourth detection position;

5) moving a part of the object that has been detected by PET completely out of the PET detector, detecting the next part of the object using the PET detector, and when any part of the object is located in the CT machine at the same time of PET detection, performing CT detection simultaneously; and performing these operations repeatedly until the object is completely moved out of the CT machine from the other side; and 6) recording all the PET data and CT data obtained, and calculating whole-body PET image data and whole-body CT image data.

12. The whole-body PET-CT combined detection method according to claim 11, wherein:

when in the first detection position, all the detection surfaces of the top detector are completely exposed, and when in the third detection position, all the detection surfaces of the neck detector are completely exposed;

the object being approximately coaxial with the CT detector and the barrel detector means that the coaxiality of the three is within 3-5 mm;

the height of the detection bed is adjusted by the lifting part by means of manual rotation or electronically controlled hydraulic pressure;

the timing when the head end of the object moves to the head position is obtained by naked eye observation or by photoelectric switch detection; and when calculating the whole-body PET image data and the whole-body CT image data, specifically, for each PET detection and CT detection, an image is obtained separately and a relative position of front and rear ends of the object corresponding to the image is recorded, and only one of the overlapping image parts is reserved, thus generating whole-body image data.

* * * * *